US010060879B2

(12) United States Patent
Silveira (10) Patent No.: US 10,060,879 B2
(45) Date of Patent: Aug. 28, 2018

(54) ION STORAGE FOR A MOBILITY SEPARATOR OF A MASS SPECTROMETRIC SYSTEM

(71) Applicant: Bruker Daltonics, Inc., Billerica, MA (US)

(72) Inventor: Joshua Silveira, Nashua, NH (US)

(*) Notice: Subject to any disclaimer, the term of this patent is extended or adjusted under 35 U.S.C. 154(b) by 0 days.

(21) Appl. No.: 15/140,554

(22) Filed: Apr. 28, 2016

(65) Prior Publication Data
US 2017/0315092 A1    Nov. 2, 2017

(51) Int. Cl.
*G01N 27/62*    (2006.01)
*H01J 49/00*    (2006.01)
*H01J 49/06*    (2006.01)

(52) U.S. Cl.
CPC ........ *G01N 27/622* (2013.01); *H01J 49/0031* (2013.01); *H01J 49/062* (2013.01)

(58) Field of Classification Search
USPC ........................................................ 250/282
See application file for complete search history.

(56) References Cited

U.S. PATENT DOCUMENTS

| 5,905,258 | A | 5/1999 | Clemmer et al. |
| 6,630,662 | B1* | 10/2003 | Loboda ................ G01N 27/622 250/281 |
| 6,639,213 | B2 | 10/2003 | Gillig et al. |
| 6,791,078 | B2 | 9/2004 | Giles et al. |
| 6,818,890 | B1 | 11/2004 | Smith et al. |
| 6,906,319 | B2* | 6/2005 | Hoyes ................... H01J 49/004 250/281 |
| 7,838,826 | B1 | 11/2010 | Park |
| 8,766,176 | B2* | 7/2014 | Park ..................... G01N 27/626 250/281 |

* cited by examiner

*Primary Examiner* — Phillip A Johnston
(74) *Attorney, Agent, or Firm* — Benoit & Côté Inc.

(57) ABSTRACT

The invention relates to methods and instruments for combined separation of ions according to mobility and mass to charge ratio. The mass spectrometric system comprises an ion source, a mobility separator and a mass analyzer wherein the mobility separator comprises (i) a gas filled drift region with a substantially constant electric DC field or a traveling electric field and (ii) an ion storage located adjacent to the entrance or inside the drift region. The ion storage comprises an electric field gradient and a gas flow wherein the electric field gradient and gas flow provide opposing forces on ions in the ion storage such that they are trapped at mobility dependent positions inside the ion storage.

20 Claims, 4 Drawing Sheets

ION STORAGE FOR A MOBILITY SEPARATOR OF A MASS SPECTROMETRIC SYSTEM

BACKGROUND OF THE INVENTION

Field of the Invention

The invention relates to methods and devices for combined measurements of ion mobility and mass spectra or combined separation of ions according to ion mobility and mass to charge ratio respectively.

Description of the Related Art

Several ion species, such as monomers and dimers, but also ions of several molecular configurations (isomers) of the same substance, are usually formed in an ion source from molecules present in a sample. Every ion species has a characteristic mobility. Isomeric ions with the same charge-related mass m/z but different collision cross-sections have different mobility in a gas of the same temperature, pressure and composition. Isomers of the smallest geometric collision cross-section possess the greatest mobility and therefore the highest drift velocity $V_d$ through the gas. Unfolded protein ions undergo more collisions than tightly folded proteins. Protein ions which are unfolded or partially folded therefore encounter more collisions and arrive at the end of the drift region later than strongly folded ions of the same mass. But structural isomers, for example proteins with glycosyl, lipid or phosphoryl groups at different sites, also have different collision cross-sections, which allows them to be distinguished by measuring their mobility.

U.S. Pat. No. 5,905,258 (Clemmer et al.) discloses a hybrid ion mobility and time-of-flight mass spectrometer comprising an ion source coupled to a mobility separator which feeds ions separated in time according to mobility directly to an ion accelerating region of a time-of-flight mass analyzer. The ions are generated in the ion source and transferred to the mobility separator. The mobility separator is operated by injecting a pulse of ions into the drift region which is filled with a gas and comprises a substantially constant (uniform) electric field along its axis. The ion pulse is generated by a gating device which is located at the entrance of the drift region and capable of injecting ions into the drift region for only a short time span of typically less than a few hundred microseconds. The injected ions are dragged through the gas by the constant electric field. The friction with the gas results in a constant drift velocity $v_d$ for each ion species that is proportional to the electric field strength E: $v_d = \mu \cdot E$. The proportionality factor $\mu$ is called the "ion mobility coefficient" of the ion species. The mobility $\mu$ is a function of gas temperature, gas pressure, type of gas, ion charge and, in particular, the ion neutral collision cross-section.

This kind of drift type mobility separator can be operated at pressures between approximately 10 Pa and more than atmospheric pressure. At low pressures between 10 Pa and 2000 Pa, the length of the drift region is typically one to four meters and the electric field strength is between one to three kilovolts per meter. The drift times of ions are typically about 1 to 100 milliseconds. In contrast to mobility separators which are operated at atmospheric pressure, the formation of complex ions by reactions with the drift gas, or impurities contained in the drift gas, is very low at low pressures and can be neglected. This fact makes low pressure ion mobility spectrometry capable to precisely determine ion-neutral collision cross sections. Furthermore, low pressure ion mobility spectrometers can be more easily coupled with mass analyzers operating under vacuum.

The mobility resolution is defined as $R = \mu/\Delta\mu = v_d/\Delta v_d$, where $\Delta\mu$ is the width of the ion signal at half height, and $\Delta v_d$ is the correspondent difference in velocity. The mobility resolution R of a mobility separator with a constant electric drift field is predominantly influenced by the electric field strength, the ion charge state, the temperature and the duration of the ion injection. Other effects, such as space charge and electric field inhomogeneity normally tend to be negligibly small.

Figure 1:
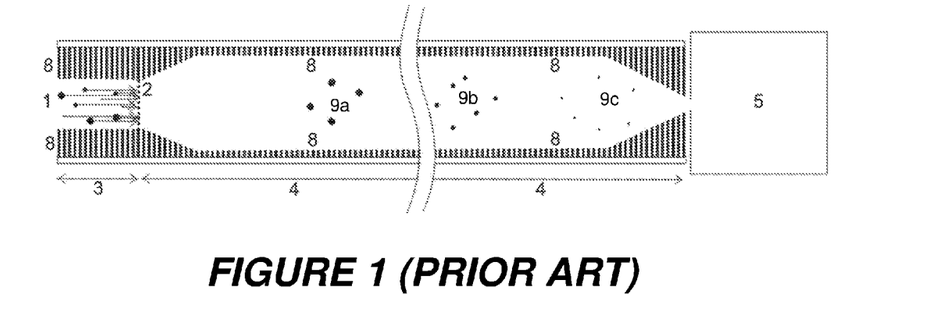

FIG. 1 shows a drift type mobility separator with a drift tube (4) and Bradbury-Nielsen grid (2) as gating device. The Bradbury-Nielsen grid (2) comprises bipolar grids with positive/negative DC voltages. Ions (1) from an ion source (not shown) are guided toward the bipolar Bradbury-Nielsen grid (2) and stopped there by discharging at the Bradbury-Nielsen grid (2). If the bipolar DC voltages at the Bradbury-Nielsen grid (2) are switched off, part of the ions are transmitted through the Bradbury-Nielsen grid (2) and enter the drift tube (4). During the drift, the ion species (9a, 9b, 9c) are separated in time according to their different drift velocities. The drift tube electrodes (8) typically have a wide inner diameter and allow injected ions (9a, 9b, 9c) to expand radially by diffusion in the gas. The separated ion species (9a, 9b, 9c) are guided to a downstream mass analyzer (5). A disadvantage of using a Bradbury-Nielsen grid (2) as a gating device is that only a small fraction of the ion population (1) is transferred to the entrance of the drift tube (4), injected into the drift tube (4) and further analyzed.

Higher utilization of ions, and thus a better sensitivity, can be achieved by trapping ions in an ion storage device located in front of the drift tube and injecting ions from the ion storage device into the drift tube. The trapping of ions at the entrance of a drift-type mobility separator is disclosed in the U.S. Pat. No. 5,905,258.

Figure 2:
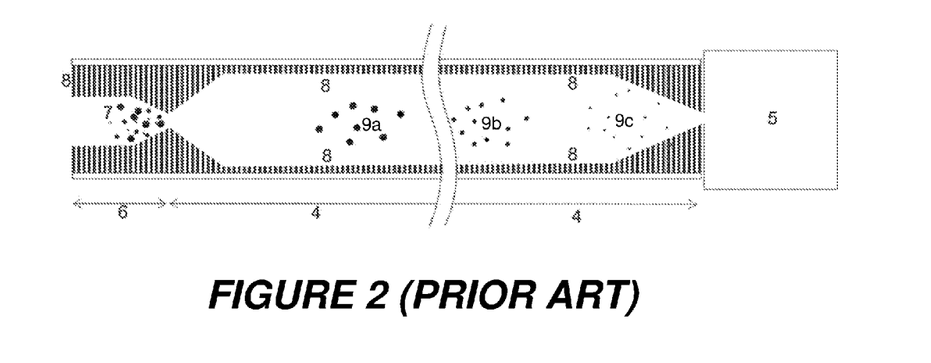
FIG. 2 shows another hybrid mobility-mass spectrometric system according to the prior art that comprises an RF ion funnel (6) as ion storage at the entrance of the drift region (4). Ions (7) transferred from an ion source (not shown) are trapped within the RF ion funnel (6) and pulsed out into the drift region (4).

U.S. Pat. No. 6,818,890 (Smith et al.) discloses a drift-type mobility separator with a specific ion storage device at the entrance of a drift tube. FIG. 2 shows a schematic of this drift-type mobility separator. The specific ion storage is an RF ion funnel (6). The ion population (7) transferred from ion source to the entrance of the drift tube (4) is trapped within the RF ion funnel (6), and pulsed out into the drift tube (4) within a short time span of typically less than a millisecond. Within the trapping region of the RF ion funnel (6), the electrodes (8) are operated by a superposition of RF and DC voltages. The RF voltages keep the ions away from the electrodes (8), and the DC voltages push the ions towards the opening of the funnel. The ions can be accumulated in the RF ion funnel (6) during the time in which previously injected ions drift through the drift tube (4). By regulating the DC and/or RF voltages, the RF ion funnel (6) can be closed or opened to release ions from RF ion funnel (6) into the drift region (4). During the drift, the ion species (9a, 9b, 9c) are separated in time according to their different drift velocities. The drift tube electrodes (8) typically have a wide inner diameter and allow the ions (9a, 9b, 9c) to expand radially by diffusion in the gas. A second RF ion funnel (not shown) can be located at the end of the drift tube (4) in order to refocus the radially expanded and separated ions (9a, 9b, 9c) on the axis of drift tube (4). The separated ion species (9a, 9b, 9c) are guided to a downstream mass analyzer (5).

U.S. Pat. No. 6,639,213 (Gillig et al.) discloses drift-type mobility separators that use periodic focusing electric DC fields in order minimize the spatial spread of migrating ions by keeping them in a tight radius about the axis of travel. The periodic focusing electric DC fields are substantially constant in time.

U.S. Pat. No. 6,791,078 (Giles et al.) discloses a different type of mobility separator. Unlike the drift-type mobility separators which utilize a constant electric field across the entire drift region, the travelling wave mobility separator consists of a stacked-ring RF ion guide that applies a repeating sequence of transient DC voltages with a specific wave height, speed, and velocity to the ring electrodes.

Ions from an ion source are transferred to an ion storage device at the entrance of the travelling wave mobility separator. Like the drift type mobility separator, the travelling wave mobility separator is operated by injecting a pulse of ions into a drift region. The transient DC voltages generate a traveling electric field that propels the injected ions through the gas filled drift region. The drift time it takes for an ion to drift through the drift region depends on its mobility as well as the wave height, speed, velocity, as well as the gas pressure. Ion species with high mobility are better able to keep up with traveling waves and are pushed more quickly through the drift region. Ion species with low mobility crest over the waves more often and have to wait for subsequent waves to push them forward, resulting in longer drift times. The different ion species, separated in time according to their mobility, are guided to a downstream mass analyzer which is typically a time-of-flight mass analyzer with orthogonal ion injection.

The resolution of a traveling wave mobility separator is affected by the travelling wave height, speed, and velocity, the gas pressure and also by the duration of ion injection.

There is still a need for methods and devices for effectively trapping and injecting ions into the drift region of a drift-type or traveling wave mobility separator, in particular, in case of high ion currents from the ion source and thus, high space charge in the trapping region. The number of injected ions should be higher than in devices according to the state of the art without sacrificing the mobility resolution of the mobility separator.

SUMMARY OF THE INVENTION

In accordance with a first aspect of the present invention, a mass spectrometric system comprises an ion source, a mobility separator and a mass analyzer. The mobility separator comprises (i) a gas filled drift region extending along an axis with a substantially constant electric DC field, a periodic focusing electric DC field or a traveling electric field and (ii) an ion storage located adjacent to or in the entrance of the drift region. The ion storage comprises an electric field gradient and a gas flow wherein the electric field gradient and gas flow extend along the axis of the drift region and provide opposing forces on ions transferred from the ion source to the ion storage device. The mobility separator is typically located between the ion source and the mass analyzer.

The ion storage and/or the drift region of the mobility separator preferably comprise a set of electrodes and a RF generator for supplying electric RF potentials of different phases to adjacent electrodes. The electric RF field generated by supplying the electric RF potentials to the electrodes generates a multipolar electric RF field that confines ions within ion storage and/or the drift region. The set of electrodes can comprise one of segmented rods and a stack of aperture-like coaxial electrodes, divided into segments. Preferably, the set of electrodes generates a substantially quadrupolar electric RF field that confines ions near the axis of drift tube. In this case, the aperture-like coaxial electrodes can be divided into quadrants wherein opposite phases of the electric RF potential are applied to adjacent quadrants.

The drift region is preferably larger than the ion storage along the axis. The drift region can be two times and even 10 times larger than the ion storage. The drift region is preferably longer than 20 cm and typically shorter than 150 cm. The pressure in the drift region is typically between 10 Pa and 2000 Pa. The ion storage can have length of up to 10 cm or even more. The drift region can have a linear or cyclic geometry.

The ion storage device can be adjacent to the entrance or inside the mobility separator. The gas flow can be directed towards the exit of the drift region. More preferably, the gas flow is directed away from the exit of the drift region.

The mass analyzer can be one of time-of-flight with orthogonal ion injection, electrostatic ion trap, RF ion trap, quadrupole mass filter, or ion cyclotron frequency. The ion source can be one of electrospray ion source (ESI), matrix-assisted laser desorption/ionization source (MALDI), electron impact (EI), or chemical ionization (CI) ion source. The mass spectrometric system can further comprise a fragmentation cell between the mobility separator and the mass analyzer as well as a mass filter between the mobility separator and the fragmentation cell.

In accordance with a second aspect of the present invention, a method for operating a mass spectrometric system comprises the steps: (a) generating ions in an ion source; (b) transferring ions from the ion source into an ion storage device located adjacent to or inside the entrance of a mobility separator, said ion storage comprising an electric field gradient and a gas flow along the axis of the mobility separator; (c) trapping ions at positions along the axis which depend on their mobility by setting the electric field gradient and the gas flow such that opposing forces act on the ions along the axis; (d) adjusting the electric field gradient and/or the gas flow to release trapped ions into the drift region of the mobility separator, said drift region comprising a substantially constant electric DC field, a periodic focusing electric DC field or a traveling electric field; (e) separating ions in time according to their mobility in the drift region; and (f) analyzing at least some of the ions separated according to mobility in a downstream mass analyzer. In case that the ions are continuously generated in the ion source, the transfer of ions is stopped prior to step (d).

In one embodiment, the electric field gradient drives the ions upstream away from the exit of the mobility separator and the gas flow drags the ions downstream towards the exit such that ions of low mobility are trapped more downstream along the axis than ions of high mobility. The ion species with the lowest mobility are trapped next to the drift region and the ion species with highest mobility are trapped farther from the drift region. This spatial order of ion species has to be reversed during the separation in the drift region of the drift-type and traveling wave mobility separator which may reduce the achievable mobility resolution to some extent.

In another embodiment, the electric field gradient drives the ions in step (c) downstream towards the exit of the mobility separator and the gas flow drags the ions upstream away from the exit such that ions of high mobility are trapped more downstream along the axis than ions of low mobility. The term "more downstream along the axis" means closer to the exit of the mobility separator. In step (d), the upstream gas flow can be reduced or stopped and/or the electric field gradient can be increased to release trapped ions into the drift region of the mobility separator.

In case that the electric field gradient is not pulsed, but slowly increased for example over several tens of milliseconds, ion species of high mobility are released first, followed by ion species of lower mobility such that the ejection time at which different ion species are injected into the drift region can be controlled. This mode of operation can provide higher resolving power for ion species that cannot be separated using the pulsed mode of operation. The electric field gradient and/or the velocity of the gas flow can be scanned linearly or non-linearly with time. The scanned or pulsed injection can also be adjusted such that not all ion species are injected into the drift region (high/low pass filter).

Optionally or additionally, another adjustable electric field can be switched on in step (d) that drives the ions from the ion storage downstream towards the drift region of the mobility separator. Preferably, the additional electric field is the constant electric DC field, the periodic focusing electric DC field or the traveling electric field of the drift region. When the additional electric field is switched on, the gas flow and/or the electric field gradient may be switched off.

Compared to trapping techniques known from prior art, methods and devices according to the present invention enable the injection of more ions into the drift region per single injection without scarifying the mobility resolution. According to the present invention, the ion species are trapped at mobility dependent positions in the ion storage. Since the spatial spread of the trapped ion species is comparable or even smaller than the initial spatial spread according to the prior art, the achievable mobility resolution of a drift-type or travelling wave mobility separator is comparable or even better using the trapping techniques of the present invention.

Furthermore, the ion storage according to the present invention exhibits a higher space charge capacity because the ion species are trapped at mobility depending positions so that the trapping volume can be extended compared to prior art.

The present invention provides methods and devices for combined separation of ions according to ion mobility and mass to charge ratio wherein the parameters of the mobility separator, like the resolving power, duty cycle or range of analyzed mobility, can be varied by a TIMS device operated upstream of the mobility separator.

BRIEF DESCRIPTION OF THE DRAWINGS

FIG. 1 shows a schematic of a hybrid mobility-mass spectrometric system according to the prior art. The mass spectrometric system comprises a gas filled drift tube (4) of a drift-type mobility separator with a Bradbury-Nielsen grid (2) at the entrance of the drift region (4). In the transfer region (3) and the drift region (4), an electric field, generated by electrodes (8), drives ions (1) from the ion source through both regions (3, 4). By applying a bipolar DC voltage to Bradbury-Nielsen grid (2), ions (1) transferred from an ion source (not shown) into the transfer region (3) are discharged at the Bradbury-Nielsen grid (2) for most of the time. In case the bipolar DC voltage is switched off for a short time period, a pulse of ions enters the drift region (4). The drift region (4) is usually composed of electrodes (8), separated from each other by insulators. A voltage divider consisting of individual resistors supplies the electrodes (8) with electric DC potentials that create a uniform electric field in the drift region (4). Ion species of different mobilities (9a, 9b, 9c) are pushed by the uniform electric field through the drift region (4) and get separated according to their mobilities. The separated ion species (9a, 9b, 9c) are sequentially guided to a downstream mass analyzer (5).

FIG. 4 shows a first embodiment according to the present invention. The electrode configuration of a TIMS device is located at the entrance of the drift region (4) of a drift-type or travelling wave mobility separator and used as an ion storage device for the mobility separator. Ions are trapped along an electric field gradient at mobility dependent positions along the separation axis.

FIG. 5 shows a second embodiment according to the present invention. The electrode configuration of a TIMS device is located at the entrance of the drift region (4) of a drift type or travelling wave mobility separator and used as a ion storage for the mobility separator. Ions are trapped along an electric field gradient at mobility dependent positions, but in a reversed spatial order compared to the embodiment shown in FIG. 4.

FIG. 6 shows a third embodiment of the present invention. The electrode configuration of a TIMS device is located at the entrance of the drift region (4) of a drift type or travelling wave mobility separator and used as an ion storage device for the mobility separator. Gas (38) is introduced at the exit of the drift region (4) and flows slowly through the drift tube (4) away from the exit toward the trapping region (32). Ions (39) from an ion source (not shown) are entrained in an additional gas flow (34) which is radially introduced at a position between the trapping region (32) and the drift region (4). The spatial order of the ion species (39) trapped in the RF tunnel (32) corresponds to the spatial order of the ion species after injection and separation in the drift region (4).

FIG. 7 shows a fourth embodiment of the present invention. The electrode configuration of a TIMS device is located at the entrance of the drift region (4) of a drift type or travelling wave mobility separator and used as an ion storage device for the mobility separator. Gas (48) is introduced at the exit of the drift region (4) and flows slowly through the drift tube (4) away from the exit toward the trapping region (42). Ions from an ion source (not shown) are entrained by gas flow (44) and axially introduced into the trapping region (42). The spatial order of the ion species (49) trapped in the RF tunnel (42) corresponds to the spatial order of the ion species after injection and separation in the drift region (4).

DETAILED DESCRIPTION

The present invention relates to hybrid mass spectrometric systems which combine a mobility separator and a mass analyzer, and methods for operation of the mass spectrometric systems. The mobility separators are drift type mobility separators with a constant electric field, or travelling wave mobility separators.

Figure 3:
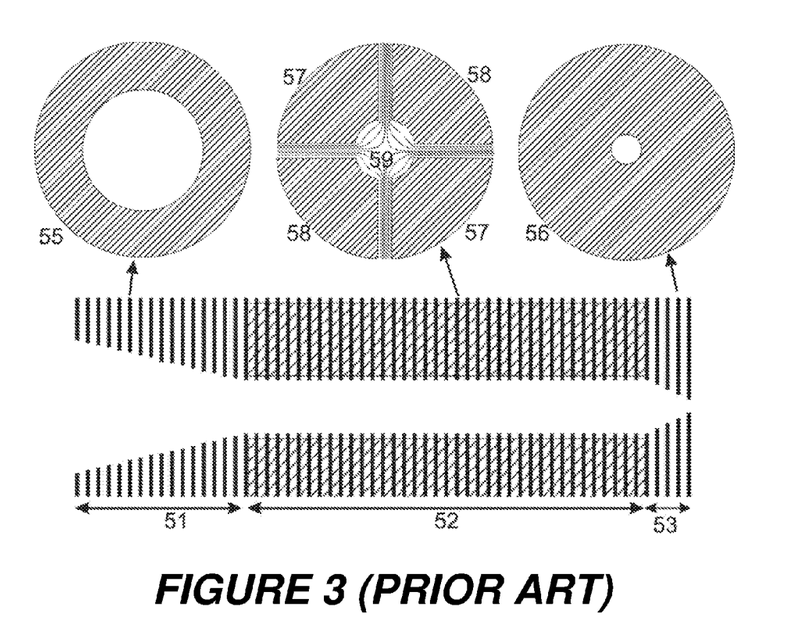
FIG. 3 shows a typical electrode configuration of a "trapping ion mobility spectrometer" (TIMS) of the type disclosed in U.S. Pat. No. 7,838,826 (Park).

FIG. 3 shows a typical electrode configuration of a "trapping ion mobility spectrometer" (TIMS) of the type disclosed in U.S. Pat. No. 7,838,826 (Park). The devices of the present invention preferably utilize a TIMS device as an ion storage device at the entrance of a drift-type mobility or traveling wave mobility separator. These ion storage devices can have a length of up to ten centimeters or more.

The electrodes of the TIMS device form a first RF funnel (51), a RF tunnel (52) with RF quadrupolar field and a second RF funnel (53). The funnels (51, 53) are built from electrodes having apertures of decreasing diameter. By supplying two phases of an RF voltage to adjacent electrodes, an electric pseudo-field is formed capable of guiding ions into the RF tunnel (52). The electrodes of the RF tunnel (52) are divided into quadrants (57, 58) respectively. By applying RF voltages of opposite phase to adjacent segments, a quadrupolar RF field (59) is generated inside the RF tunnel (52), capable of holding ions near the axis. However, the quadrupolar field can in principle be replaced by any multipolar field. At the same time, an electric field gradient profile can be generated along the axis of the RF tunnel (52) by applying DC voltages to the electrodes.

The TIMS device can be used for ion storage in which ion species are trapped at positions along the axis of the TIMS device which depend on the mobility of the trapped ion species. In operation, a gas flow drives ions in the RF tunnel (52) against a counteracting electric field gradient. An ion population transferred from an ion source to the TIMS device is separated into bunches of ions along the electric field gradient wherein each ion bunch has the same mobility. By changing for example the electric field gradient, the trapped ion species can be released from the TIMS device and injected into a mobility separator.

Figure 4:
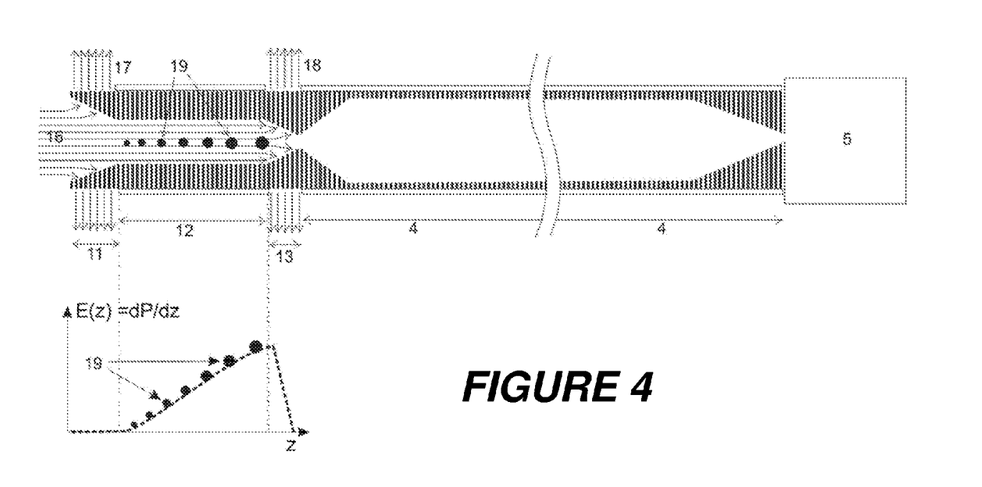

FIG. 4 shows a first embodiment according to the present invention. The electrode configuration of a TIMS device is located at the entrance of the drift region (4) of a drift type or travelling wave mobility separator and used as a ion storage for the mobility separator.

The ion storage region comprises a first RF funnel (11), a tube-like RF tunnel (12) and second RF funnel (13). The RF tunnel (12) is formed by quadrupolar electrodes, as shown for the tunnel (52) in FIG. 3, capable of generating a radial quadrupolar RF field superimposed by an axial electric DC field. Ions entrained in a gas stream (16) enter the TIMS device and are focused on the axis by the quadrupolar RF field of the RF tunnel (12). The electric field profile E(z) along the axis of the RF tunnel (12) is shown in the lower part of FIG. 4. A quadratic increase of the electric potential P(z) along the axis can for example form a linear ramp. However, the electric field at the ramp does not necessarily need to be linear as a function of position.

The laminar gas flow (16) drives the ions against an electric field gradient (ramp) of the profile E(z) whereby the ion species are spatially separated into bunches of ions (19) of the same mobility. Ion species of low mobility are stopped by higher electric field at the end of the ramp, whereas ion species of high mobility are already stopped at the beginning of the ramp. The spatial spread of the ion bunches during trapping in the RF ion tunnel (12) is typically only on the order of one to two millimeters. As an example, the gas flow may have a velocity of 50 to 150 meters per second, and the maximum field strength E(z) may amount to 30 to 90 volts per centimeter. The gas flow (16) is directed downstream towards the exit of the drift region (4) and leaves the mobility separator at the second RF funnel (13) before entering the drift region (4).

Switching off or reducing the electric field gradient or even reversing the electric field gradient, blows the trapped ion species (19) into the drift region (4). This device delivers much smaller ion bunches than the devices of FIGS. 1 and 2. However, the spatial order of trapped ion species (19) is reversed during the drift in the drift region (4) whereby the faster ions of high mobility have to pass the slower ions of low mobility. Since a part of the drift region (4) is needed to reverse the spatial order of the trapped ion species (19), the mobility separator does not achieve the maximum mobility resolution. In addition, the ion bunches may influence each other during the passages by space charge effects, again reducing ion mobility resolution. After passing the drift region (4), the ion species separated in time according to mobility are sequentially guided to a downstream mass analyzer (5).

Figure 5:
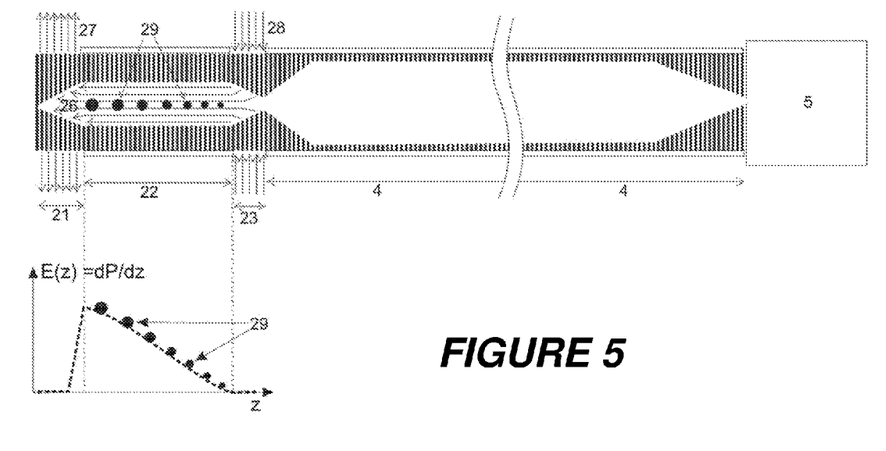

FIG. 5 shows a second embodiment according to the present invention. The electrode configuration of a TIMS device is located at the entrance of the drift region (4) of a drift-type or travelling wave mobility separator and used as an ion storage device for the mobility separator. Compared to the embodiment of FIG. 4, ions are again trapped along an electric field gradient at mobility dependent positions, but in a reversed spatial order.

Ions from an ion source (not shown) are entrained in an inflowing gas (28) and trapped in the RF tunnel (22). Gas exits the region (21) as outflowing gas (27). In region (21), the electrodes are formed as a funnel to generate an undisturbed gas flow in the RF tunnel (22). The electric field profile E(z) along the axis of the RF tunnel is shown in the lower part of FIG. 5. The gas flow (26) drives the ions (29) against an electric field gradient (ramp) of the profile E(z). The gas flow (26) is directed away from the exit of the drift region (4) whereas the electric field gradient pushes the ions towards the exit of the drift region (4). Ion species of high mobility are stopped at the beginning of the ramp, whereas ion species of low mobility are stopped by higher electric field at the end of the ramp. The spatial order of the ion species (29) during trapping along the electric field gradient is preserved during the separation in the drift region (4).

By reducing or stopping the gas flows (27, 28) or by increasing the field strength of the electric field gradient, the trapped ion species (29) are ejected as ion bunches into the long drift region (4). The ion species separated in time in the drift region (4) are subsequently guided to a mass analyzer (5) and analyzed according their mass to charge ratio.

Figure 6:
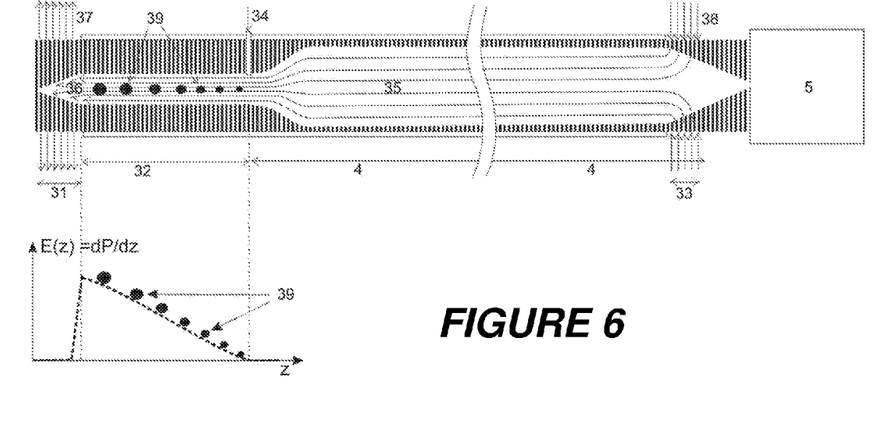

FIG. 6 shows a third embodiment of the present invention. The electrode configuration of a TIMS device is located at the entrance of the drift region (4) of a drift type or travelling wave mobility separator and used as an ion storage device for the mobility separator.

Compared to the embodiment shown in FIG. 5, the gas flow system is slightly different in this embodiment. Gas (38) is introduced at the exit of the drift region (4) and flows slowly through the drift tube (4) away from the exit toward the trapping region (32). The gas velocity in the trapping region (32) is increased because the electrode diameter in the trapping region (32) is reduced compared to the electrode diameter in the drift region (4). Ions (39) from an ion source (not shown) are entrained in an additional gas flow (34) which is radially introduced at a position between the trapping region (32) and the drift region (4). The electric field profile E(z) along the axis of trapping region (32) is shown in the lower part of FIG. 6. The gas flow (36) drives the ions (39) against an electric field gradient (ramp) of the profile E(z). The spatial order of the ion species (39) trapped in the RF tunnel (32) corresponds to the spatial order of the ion species after injection and separation in the drift region (4). The ion bunches (39) can be released into the drift region (4) by increasing the field strength of the electric field gradient or by reducing the gas flows (37, 38). The ion species separated in time in the drift region (4) are subsequently guided to a mass analyzer (5) and analyzed according their mass to charge ratio.

Figure 7:
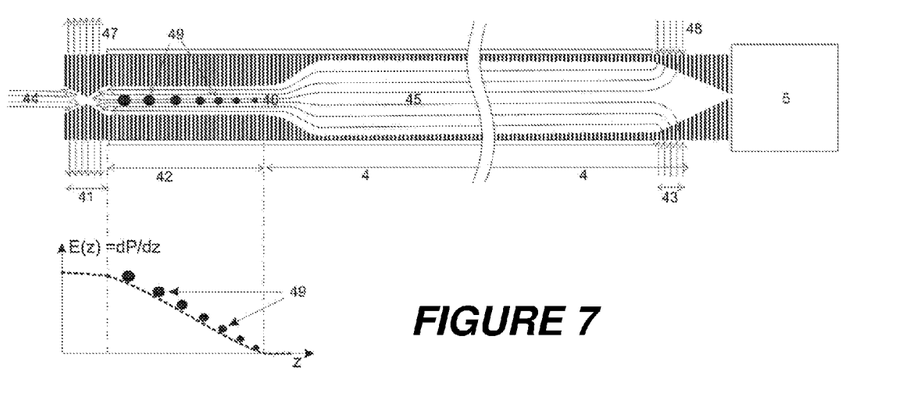

FIG. 7 shows a fourth embodiment of the present invention. The electrode configuration of a TIMS device is located at the entrance of the drift region (4) of a drift type or travelling wave mobility separator and used as an ion storage for the mobility separator.

Gas (48) is introduced at the exit of the drift region (4) and flows slowly through the drift tube (4) away from the exit toward the trapping region (42). The gas velocity in the trapping region (42) is increased because the electrode diameter in the trapping region (42) is reduced compared to electrode diameter in the drift region (4). Ions from an ion source (not shown) are entrained by gas flow (44) and axially introduced into the trapping region (42). An RF hourglass-funnel disclosed in U.S. Pat. No. 6,818,890 (Smith et al.) with alternately supplied phases of an RF voltage and a DC driving force transports the ions from gas flow (44) into the RF tunnel (42). The spatial order of the ion species (49) trapped in the RF tunnel (42) corresponds to the spatial order of the ion species after injection and separation in the drift region (4). The ion bunches (49) can be released into the drift region (4) by increasing the field strength of the electric field gradient or by reducing the gas flows (47, 48). The ion species separated in time in the drift region (4) are subsequently guided to a mass analyzer (5) and analyzed according their mass to charge ratio.

Compared to prior art trapping devices, the ion storage devices shown in embodiments of FIGS. 5-7 release at the same time smaller ion bunches and more ions into the drift region (4) wherein the ion bunches are already spatially aligned in the same spatial order that the ion species have after separation in the drift region (4). Therefore, the sensitivity as well as the mobility resolution is increased compared to the prior art instruments. Furthermore, the trapping volume is increased and thus the influence of space charge is reduced.

The spatial spread of an ion bunch during storage, according to the present invention, can be calculated by the following equation:

$$FWHM_z = \sqrt{\frac{8\ln 2 k_b T}{q} \cdot \frac{KL}{v_g}},$$

wherein $FWHM_z$ is the spatial distribution of the trapped ion species, K is the ion mobility coefficient, L is the axial length of the ion storage, q the charge of the ion species, T the temperature of the gas, $k_b$ is the Boltzmann constant and $v_g$ is the gas velocity. The prior art instruments shown in FIGS. 1 and 2 are presently using a typical gate width b etween 100-500 microseconds. Assuming that an ion species moves at a velocity of about 50 m/s in a drift type or travelling wave separator, this yields an estimated initial spatial spread of 5 to 25 mm when entering the drift region after gating. For typical ion storages according to the present invention, a gas velocity of 50 m/s gas flow at 3 mbar and a length of 5 cm can be estimated. At a minimum, the initial spatial distribution of injected ion species would be smaller by a factor of four.

For a drift type mobility separator operated with 3000 volts applied across the drift tube and an ion species with a 50 milliseconds drift time, the mobility resolution for a gate width of 500 microseconds is lower than the diffusion limit by ~30% due to the effect of the gate width (R=102 for a delta pulse vs. R=71 using a gate witdh). An improvement in the gate width by a factor of four yields a resolving power of 99 that very closely approximates a delta pulse. The added advantage of the present invention is that while the mobility resolution closely matches the diffusion limited result, all of the trapped ions can be pulsed into the drift tube in a single injection thereby increasing the duty cycle. Furthermore, the resolution can even be increased above the diffusion limit if the electric field upon injection is scanned in time yielding additional temporal separation.

The mass analyzer (5) shown in FIGS. 1, 2 and 4-7 can be one of time-of-flight with orthogonal ion injection, electrostatic ion trap, RF ion trap, or ion cyclotron frequency and quadrupole mass filter. The ion source can be one of an electrospray ion source (ESI), matrix-assisted laser desorption/ionization source (MALDI), electron impact (EI) ion source and chemical ionization (CI) ion source. The mass spectrometric system can further comprise a fragmentation cell between the mobility separator and the mass analyzer and a mass filter between the mobility separator and the fragmentation cell.

The invention claimed is:

1. A mass spectrometric system comprising:
   an ion source;
   a mobility separator, said mobility separator comprising:
   (i) a gas filled drift region in which ions are separated by mobility, the drift region extending along an axis and having one of a substantially constant electric DC field, a periodic focusing electric DC field or a traveling electric field; and
   (ii) an ion storage that separates stored ions by mobility and that is located adjacent to or in the entrance of the drift region; and
   a mass analyzer,
   wherein the ion storage comprises an electric field gradient and a gas flow, said electric field gradient and gas flow extending along the axis of the drift region and providing opposing forces on ions transferred from the ion source to the ion storage that trap and separate the ions along the axis.

2. The mass spectrometric system according to claim 1, wherein the mobility separator is located between the ion source and the mass analyzer.

3. The mass spectrometric system according to claim 1, wherein the ion storage and/or the drift region of the mobility separator comprise a set of electrodes and an RF generator for supplying electric RF potentials of different phases to adjacent electrodes.

4. The mass spectrometric system according to claim 3, wherein the set of electrodes are one of segmented rods and a stack of aperture-like coaxial electrodes, divided into segments.

5. The mass spectrometric system according to claim 1, wherein the drift region is larger than the ion storage along the axis.

6. The mass spectrometric system according to claim 5, wherein the drift region is longer than 20 cm.

7. The mass spectrometric system according to claim 1, wherein the pressure in the drift region is between 10 Pa and 2000 Pa.

8. The mass spectrometric system according to claim 1, wherein the ion storage is adjacent to the entrance or inside the mobility separator and the gas flow is directed towards the exit of the drift region.

9. The mass spectrometric system according to claim 1, wherein the ion storage is adjacent to the entrance or inside the mobility separator and the gas flow is directed away from the exit of the drift region.

10. The mass spectrometric system according to claim 1, wherein the mass analyzer is one of time-of-flight with orthogonal ion injection, electrostatic ion trap, RF ion trap, or ion cyclotron frequency and quadrupole mass filter.

11. The mass spectrometric system according to claim 10, further comprising a fragmentation cell between the mobility separator and the mass analyzer.

12. The mass spectrometric system according to claim 11, further comprising a mass filter between the mobility separator and the fragmentation cell.

13. A method for operating a mass spectrometric system, comprising the steps of:
(a) generating ions in an ion source;
(b) transferring ions from the ion source into an ion storage device located adjacent to or inside the entrance of a mobility separator, said ion storage comprising an electric field gradient and a gas flow along the axis of the mobility separator;
(c) trapping and separating ions in the ion storage device at positions along the axis which depend on their mobility by setting the electric field gradient and the gas flow such that opposing forces act on the ions along the axis;
(d) adjusting the electric field gradient and/or the gas flow to release trapped ions into the drift region of the mobility separator, said drift region comprising one of a substantially constant electric DC field, periodic focusing electric DC field or a traveling electric field;
(e) separating ions in time according to their mobility in the drift region; and
(f) analyzing at least some of the ions separated according to mobility in a downstream mass analyzer.

14. The method according to claim 13, wherein, in step (c), the electric field gradient drives the ions downstream towards the exit of the mobility separator and the gas flow drags the ions upstream away from the exit such that ions of high mobility are trapped more downstream along the axis than ions of low mobility.

15. The method according to claim 14, wherein, in step (d), the upstream gas flow is reduced and/or the electric field gradient is increased to release trapped ions into the drift region of the mobility separator.

16. The method according to claim 14, wherein, in step (d), another electric field is switched on and drives the ions from the ion storage downstream towards the drift region of the mobility separator.

17. The method according to claim 16, wherein the additional electric field is substantially the constant electric DC field or a traveling electric field of the drift region.

18. The method according to claim 17, wherein the upstream gas flow and the electric field gradient are switched off when the additional electric field is switched on.

19. The method according to claim 13, wherein, in step (c), the electric field gradient drives the ions upstream away from the exit of the mobility separator and the gas flow drags the ions downstream towards the exit such that ions of low mobility are trapped more downstream along the axis than ions of high mobility.

20. A method according to claim 13, wherein the ions are continuously generated in the ion source and the transfer of ions is stopped prior to step (d).

* * * * *